(12) United States Patent
Vahcic et al.

(10) Patent No.: US 12,416,619 B2
(45) Date of Patent: Sep. 16, 2025

(54) SIMULANT COMPOSITION OF AN EXPLOSIVE COMPOUND

(71) Applicant: THE EUROPEAN UNION, REPRESENTED BY THE EUROPEAN COMMISSION, Brussels (BE)

(72) Inventors: Mitja Vahcic, Geel (BE); David Anderson, Brussels (BE); John Seghers, Ham (BE); Hanne Leys, Kasterlee (BE)

(73) Assignee: THE EUROPEAN UNION, REPRESENTED BY THE EUROPEAN COMMISSION, Brussels (BE)

( * ) Notice: Subject to any disclaimer, the term of this patent is extended or adjusted under 35 U.S.C. 154(b) by 731 days.

(21) Appl. No.: 17/770,941

(22) PCT Filed: Oct. 19, 2020

(86) PCT No.: PCT/EP2020/079336
§ 371 (c)(1),
(2) Date: Apr. 21, 2022

(87) PCT Pub. No.: WO2021/078676
PCT Pub. Date: Apr. 29, 2021

(65) Prior Publication Data
US 2022/0390428 A1    Dec. 8, 2022

(30) Foreign Application Priority Data

Oct. 24, 2019 (EP) .................... 19205191

(51) Int. Cl.
*G01N 33/22* (2006.01)

(52) U.S. Cl.
CPC .................... *G01N 33/227* (2013.01)

(58) Field of Classification Search
CPC .................................................. G01N 33/227
(Continued)

(56) References Cited

U.S. PATENT DOCUMENTS

| 3,119,705 A * | 1/1964 | Kintish | ............... G01N 33/227 |
| | | | 106/266 |
| 3,178,325 A * | 4/1965 | Scott, Jr. | ................. C06B 31/14 |
| | | | 149/69 |

(Continued)

FOREIGN PATENT DOCUMENTS

| CN | 102795951 A | 11/2012 |
| CZ | 305617 B6 * | 1/2016 |
| RU | 2 097 836 C1 | 11/1997 |

OTHER PUBLICATIONS

Bond, et al., "ZeCalc Algorithm Details", Tech. Rep. LLNL-TR-609327, Lawrence Livermore National Laboratory, Jan. 2013 (15 sheets).

(Continued)

*Primary Examiner* — Arlen Soderquist
(74) *Attorney, Agent, or Firm* — Womble Bond Dickinson (US) LLP

(57) ABSTRACT

The present invention relates to a powdered simulant composition of an explosive compound having an $Z_{eff}$ between 6.5 and 7.5 and a and the use thereof.

20 Claims, 2 Drawing Sheets

○ Cumulative Distribution $Q_3$/%

● Distribution Density $q_3^*$

(58) Field of Classification Search
USPC .............................................................. 436/8
See application file for complete search history.

(56) References Cited

U.S. PATENT DOCUMENTS

| | | | | |
|---|---|---|---|---|
| 5,359,936 | A * | 11/1994 | Simpson | .................... F42B 8/00 |
| | | | | 102/529 |
| 5,648,636 | A * | 7/1997 | Simpson | ............... F41H 11/134 |
| | | | | 102/527 |
| 5,958,299 | A | 9/1999 | Kury et al. | |
| 7,854,811 | B1 | 12/2010 | Wartman et al. | |
| 8,114,230 | B1 * | 2/2012 | Basom | ...................... F42D 5/04 |
| | | | | 149/46 |
| 9,291,436 | B2 | 3/2016 | Eshetu et al. | |
| 2006/0160914 | A1 | 7/2006 | Orpin | |
| 2007/0281358 | A1 * | 12/2007 | Cohen-Arazi | ............ F42B 8/00 |
| | | | | 436/8 |
| 2012/0180701 | A1 * | 7/2012 | Benson | ................. C04B 14/365 |
| | | | | 106/471 |
| 2013/0026420 | A1 * | 1/2013 | Duffy | ...................... C06B 23/00 |
| | | | | 252/408.1 |
| 2015/0268016 | A1 * | 9/2015 | Eshetu | ...................... F42B 8/28 |
| | | | | 434/11 |
| 2018/0060450 | A1 * | 3/2018 | McNamara | ............. G06F 30/00 |

OTHER PUBLICATIONS

Faust, et al., "*Design and validation of inert homemade explosive simulants for X-ray-based inspection systems*", Proc. SPIE 9073, Chemical, Biological, Radiological, Nuclear, and Explosives (CBRNE) Sensing XV, 90730V, May 29, 2014 (12 sheets).

International Search Report and Written Opinion for corresponding PCT Application No. PCT/EP2020/079336, mailed Feb. 9, 2021 (9 sheets).

* cited by examiner

○ Cumulative Distribution $Q_3$/%
● Distribution Density $q_3^*$

SIMULANT COMPOSITION OF AN EXPLOSIVE COMPOUND

CROSS-REFERENCE TO RELATED APPLICATIONS

This application is a National Phase Patent Application and claims priority to and the benefit of International Patent Application Number PCT/EP2020/079336, filed on Oct. 19, 2020, which claims priority to European Patent Application Number 19205191.0, filed on Oct. 24, 2019. The entire contents of both of which are incorporated herein by reference.

FIELD OF THE INVENTION

The present invention relates to a powdered simulant composition of an explosive compound and the use thereof. In particular, the present invention relates to a powdered simulant composition of an explosive compound, preferably of triacetone triperoxide, having an effective atomic number between 6.5 and 7.5. The present invention further relates to a method for producing a powdered simulant composition of an explosive compound.

BACKGROUND OF THE INVENTION

Important safety measures such as explosive detection are routinely carried out at locations having high concentration of people like airports. Explosive detection can be achieved by using X-ray transmission detection systems which are able to detect explosives by certain physical properties such as their effective atomic number ($Z_{eff}$, hereinafter) and their bulk density.

It is often necessary to verify the detection performance of such X-ray transmission detection systems. Using real explosives for such a task is impractical because it would put the user at risk. As a consequence explosive simulant compositions, which are safer than real explosives, are used in order to test X-ray transmission detection systems. As a consequence, such explosive simulant compositions should, in particular, be inert and preferably made from components of low toxicity, which when mixed together into an explosive simulant composition exhibit X-ray transmission properties as the real explosive in terms of bulk density, $Z_{eff}$. Additionally, such simulant compositions should have the same color and physical form as the explosive compound.

Many explosives such as for example TATP (triacetone triperoxide), ammonia nitrate and 2,4,6-trinitroaniline possess a $Z_{eff}$ between 6.5 and 7.5. Furthermore, poorly controlled (i.e. homemade) synthesis conditions associated with improvised explosive devices can affect the explosive properties such as its $Z_{eff}$ and bulk density. Thus, it is also important to be able to produce explosive simulant compositions covering a wide range of $Z_{eff}$ in addition to the exact value of $Z_{eff}$ associated to the real explosive. For example, in the case of homemade TATP, the $Z_{eff}$ can easily vary from 6.5 to 7.5. As a consequence, it is thus required to be able to produce explosive simulant compositions in this $Z_{eff}$ range. The bulk density may also vary in the case of homemade explosives, thus it is advantageous to be able to produce explosive simulant compositions with different bulk densities.

Moreover, the physical state of matter affects the x-ray attenuation properties of a given material. This means that the detection and behavior of liquid, solid and powder materials by x-ray equipment differs for each state. Thus the physical state of the simulant is a highly important parameter if a realistic simulant is to be created. Many explosives, such as TATP are in powder form, thus the corresponding simulant should also be in powder form. Another point of concern is the thermal stability of the explosive simulant composition. Usually, the explosive simulant compositions are used at room temperatures or bellow. However in hot climates and during transport, the temperatures can reach up to 60° C. Taking this into account, the explosive simulant compositions should be produced from components which can withstand this temperature. Thus, it is important that the explosive simulant composition remains in powder form at 60° C. and/or at least that its constituents do not melt at 60° C. since it would cause changes in the simulant composition properties.

Moreover, self-compaction of the explosive simulant compositions should be avoided because it changes properties of the explosive simulant composition such as its bulk density. However, a certain amount of compaction should be achieved in order for the explosive simulant composition to properly mimic the explosive properties (i.e. bulk density). Thus, the explosive simulant composition should be compactable enough to reach the right bulk density but should not suffer self-compaction.

Various explosive simulant compositions are known in the art. For example, U.S. Pat. No. 9,291,436 B1 discloses a TATP simulant composition consisting of polyethylene power, granulated sugar can, glycerin and sugar.

CN 102795951 discloses different TATP simulant compositions. A first formulation consists of grape acid, neopentyl glycol and salicylic acid. Another disclosed composition consists of glycolic acid, n-hexadecanol, itaconic acid. Another composition consists of grape acid, neopentyl glycol and terephthalic acid. A fourth composition is disclosed and consists of malonic acid, sebasic acid, 1-6-hexanediol.

These explosive simulant compositions do not comply with all the requirements described above. For instance, some compositions are difficult to compact or suffer from self-compaction and thus the bulk density of the explosive cannot be reached. Moreover, some of the above-mentioned compositions are not in a solid form but are a liquid or paste form and thus do not properly simulate the physical form of the explosive of interest.

In view of the above, it is clear that there is a long standing need to be able to provide a composition suitable for producing a simulant composition of an explosive compound and the simulant composition thereof which satisfies at least all of the following conditions:
- the simulant composition must exhibit the same x-ray transmission properties as real explosives (homemade or not) such as TATP, at least in terms of bulk density and $Z_{eff}$,
- the simulant composition should have the same physical appearance, meaning it must be in solid form, preferably in powder form, and preferably have the same color,
- the simulant composition and its constituents must be in a powder form, even at temperature as high as 60° C.,
- the simulant composition should not suffer from self-compaction but should be sufficiently compacted in order to possess a density substantially close to the density of the explosive compound (homemade or not).

SUMMARY OF THE INVENTION

The inventors have now surprisingly found that it is possible to provide a composition suitable for producing a simulant composition of an explosive compound and the simulant composition thereof fulfilling the above mentioned long standing need.

Thus, there is now provided a powdered composition [composition (C), hereinafter] suitable for producing a simulant composition of an explosive compound, said composition (C) has an effective atomic number [$Z_{eff}$, hereinafter] between 6.5 and 7.5 and comprises, relative to the total weight of the composition (C), a) at least 25.0% by weight (wt. %) and at most 75.0 wt. % of solid particles of at least one inert organic compound [compound (OR), hereinafter], having a general formula (I):

$$[R_1\text{-}FG]_x M^{x+} \tag{I}$$

wherein FG is a functional group selected from the group consisting of carboxylate group, a sulfate group, a sulfonate group, a benzylsulfonate ether groups, a phosphate group, an isethionate group, a sulphosuccinate group, an acyl citrate group, an acyl taurate group, an sarcosinate group, an amino carboxylate group; and wherein M is a metal M selected from the group consisting of alkali metals, alkali-earth metals and transition metals and x is 1, 2 or 3; and $R_1$ is hydrocarbon radicals comprising from 6 to 24 carbon atoms; and b) at least 25.0% by weight (wt. %) and at most 75.0 wt. % of solid particles of at least one inert compound comprising at least C, H and O elements [compound (I), hereinafter] wherein said compound (I) has a density of below 2.4 g/cm³ and a melting point of at least 40° C.

In another aspect, the present invention further provides a method for producing said composition (C).

In yet another aspect, the present invention further provides a simulant composition of an explosive compound [composition (S), hereinafter].

In yet another aspect, the present invention further provides a method for producing said composition (S).

In yet another aspect, the present invention further provides a use of said composition (S) in a X-ray scanner.

DETAILED DESCRIPTION

Figure 1:
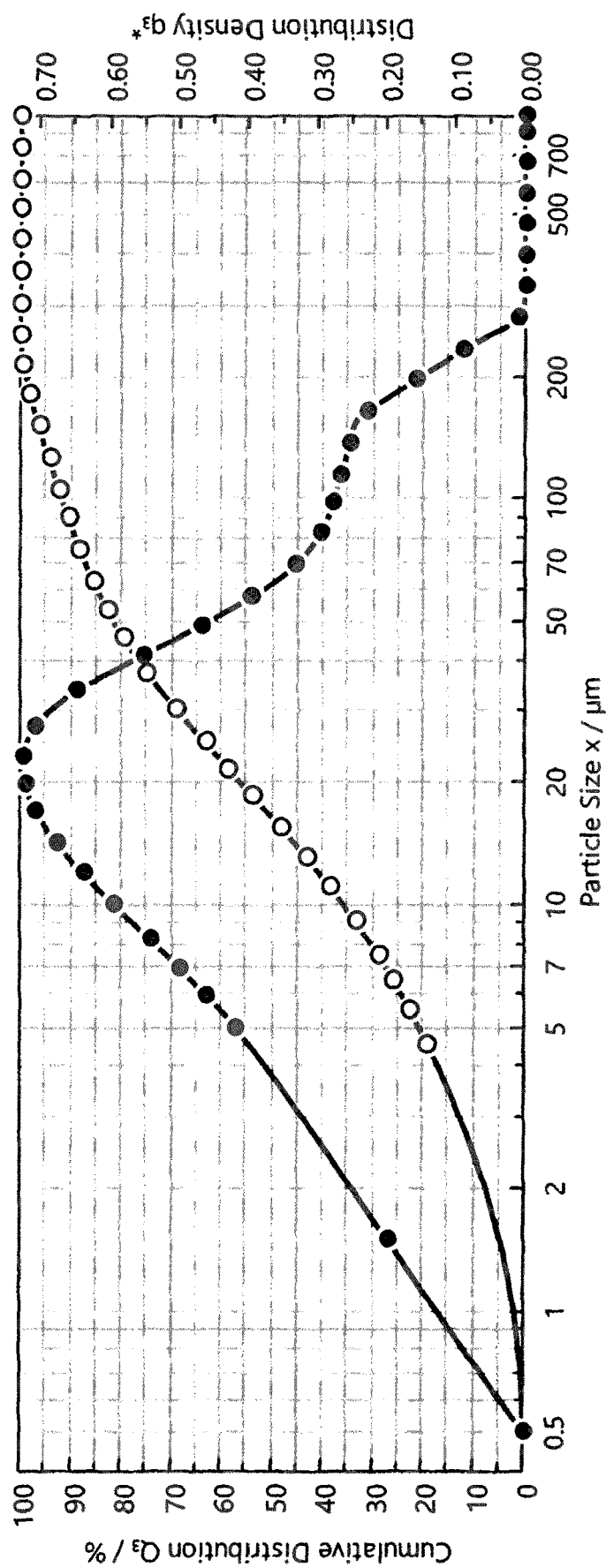
FIG. 1 shows the obtained particle size distribution of example 1.

As used herein and in the claims, the terms "comprising" and "including" are inclusive or open-ended and do not exclude additional unrecited elements, compositional components, or method steps. Accordingly, the terms "comprising" and "including" encompass the more restrictive terms "consisting essentially of" and "consisting of".

Composition (C)

Thus, as detailed hereinabove according to the present invention there is provided a composition [composition (C), hereinafter] suitable for producing a simulant composition of an explosive compound having an effective atomic number [$Z_{eff}$, hereinafter] between 6.5 and 7.5.

Thus according to the above, composition (C) has a $Z_{eff}$ between 6.5 and 7.5. Within the context of the invention, the term "effective atomic number [$Z_{eff}$, hereinafter]" describe the radiation attenuation properties of a compound or a composition. Elements with a high atomic number, Z, will attenuate x-rays (particularly lower energy X-rays) more than elements with a low Z. A compound or a composition will attenuate X-rays to a degree that is somewhere between that of the highest- and lowest-Z elements present in the composition.

The skilled in the art knows how to determine the $Z_{eff}$ of a compound or a composition. For example, the $Z_{eff}$ can be determined by using an algorithm developed by Lawrence Livermore National Laboratory (USA) in 2013. The algorithm aims at a physically meaningful definition of effective atomic number, which is calculated using the energy-dependent cross sections of the ingredients in the mixture. [LLNL-TR-609327, K. C. Bond, J. A. Smith, J. N. Treuer, S. G., Azevedo, J. S. Kallman, H. E. Martz, 2013], https://e-reports-ext.llnl.gov/pdf/650532.pdf.

Within the context of the invention, the term "explosive compound" are intended to denote any compound that can cause an explosion, a detonation or a deflagration.

Examples of such explosive compounds include but are not limited to TATP, ammonia nitrate, 2,4,6-trinitroaniline and the like, preferably, the explosive compound is TATP.

According to the present invention, the explosive compound may be a pure explosive compound or an explosive compound containing impurities. The presence of impurities in the explosive compound influences the properties of the explosive compound such as its $Z_{eff}$. Homemade explosive compounds often comprise certain level of impurities and thus their $Z_{eff}$ varies accordingly. For example in the case of TATP, the $Z_{eff}$ of impure TATP can vary between 6.5 and 7.5 depending on the amount of impurities present in the TATP.

Compound (OR)

As detailed hereinabove, the composition (C) comprises relative to the total weight of the composition (C) at least 25.0% by weight (wt. %) and at most 75.0 wt. % of solid particles of at least one inert organic compound [compound (OR), hereinafter], having a general formula (I):

$$[R_1\text{-}FG]_x M^{x+} \tag{I}$$

wherein FG is a functional group selected from the group consisting of a carboxylate group, a sulfate group, a sulfonate group, a benzylsulfonate ether groups, a phosphate group, an isethionate group, a sulphosuccinate group, an acyl citrate group, an acyl taurate group, an sarcosinate group, an amino carboxylate group; and wherein M is a metal M selected from the group consisting of alkali metals, alkali-earth metals and transition metals and x is 1, 2 or 3; and $R_1$ is hydrocarbon radicals comprising from 8 to 24 carbon atoms.

In the rest of the text, the expression "compound (OR)" is understood, for the purposes of the present invention, both in the plural and the singular, that is to say that the composition (C) may comprise one or more than one compound (OR).

Within the context of present invention, the term 'inert' is intended to mean that the at least one compound (OR) is inert in a sense that it will not explode, burn or react if exposed to air. However, it goes without saying that if exposed to acids or other reacting chemicals it will react according to functional groups present.

The inventors have now surprisingly found that the compound (OR), as detailed above, when present in the form of solid particles and in an amount from 25.0% wt. % to 75.0 wt. %, the composition (C) can be compacted in order to reach the density of the explosive compound. Indeed, more than 75 wt. % of solid particles of said compound (OR) makes the composition (C) difficult or nearly impossible to compact in order to obtain the density of the explosive compound. Without being bound to this theory, it appears that the compound (OR) being an ionic compound having positively charged ions and negatively charged ions tends to render the composition (C) difficult to compact due to the presence of too many charges (i.e. repulsive forces generated by these charges). On the other hand, the solid particles of said compound (OR) need to be present in an amount of at least 25.0 wt. % in order to prevent self-compaction. Thus, it was found that from 25.0 wt. % to 75.0 wt. % of solid particles of said compound (OR) is a good compromise in order to avoid self-compaction effects but still allow the composition (C) to be compacted in order to reach the density of the explosive compound.

According to a preferred embodiment of the present invention, the composition (C) comprises, relative to the total weight of the composition (C), the solid particles of the compound (OR) in an amount of at least 30.0 wt. %, more preferably at least 40.0 wt. %, even more preferably at least 50.0 wt. %. It is further understood that the solid particles of the compound (OR) are advantageously present in the composition (C) in a weight amount of at most 70.0 wt. %, more preferably at most 68.0 wt. % and more preferably at most 65.0 wt. %, relative to the total weight of the composition (C).

According to a preferred embodiment, said composition (C) comprises relative to the total weight of the composition (C) from 30.0 wt. % to 70.0 wt. %, preferably from 40.0 wt. % to 70.0 wt. %, more preferably from 50.0 wt. % to 70.0 wt. %, more preferably from 50.0 wt. % to 65.0 wt. % of solid particles of said compound (OR).

Good results were obtained when the solid particles of the compound (OR), as detailed above, were present from 40.0 wt. % to 70.0 wt. % relative to the total weight of the composition (C).

According to the general formula (I), FG is a functional group, preferably an anionic functional group, more preferably the anionic functional group is selected from the group consisting of a carboxylate group, a sulfate group, a sulfonate group, a phosphate group, an isethionate group, a sulphosuccinate group, an acyl citrate group and an amino carboxylate groups. Most preferably, FG is a carboxylate group.

The term "hydrocarbon radical comprising from 8 to 24 carbon atoms", as used herein, may have the broadest meaning generally understood in the art, and may include a moiety which is linear, branched, cyclic or a combination thereof which may be completely saturated or may contain one or more units of unsaturation, but which is not aromatic and all of these 8 to 24 carbon atoms may be optionally substituted.

The term "saturated", as used herein, means that a moiety has no double or triple bonds.

The term "unsaturated", as used herein, means that a moiety has one or more double or triple bonds.

Preferably, $R_1$ is a hydrocarbon radical comprising from 10 to 22 carbon atoms, more preferably from 12 to 20 carbon atoms, even more preferably from 15 to 18 carbon atoms.

Preferably, the hydrocarbon radical is saturated. Preferably the hydrocarbon radical is linear. More preferably, the hydrocarbon radical is linear and saturated.

Preferably, M is an alkali metal and x is 1 or an alkali-earth metal and x is 2, more preferably M is an alkali metal selected from the group consisting of Na, K and Li and x is 1 or M is an alkali-earth metal selected from the group consisting of Ca, Mg and Zn and x is 2.

Preferred compounds (OR) are of general formula (II):

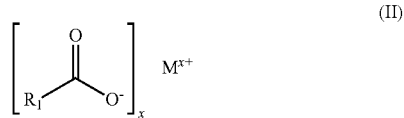

wherein $R_1$, M and x have the same meaning as defined above.

Preferred compounds (OR) according to formula (II) notably include: sodium stearate, lithium stearate, calcium stearate, magnesium stearate, zinc stearate, sodium palmitate and the like.

According to a preferred embodiment of the present invention, the composition (C) comprises, relative to the total weight of the composition (C), from 50.0 wt. % to 70.0 wt. %, preferably from 50.0 wt. % to 65.0 wt. % of solid particles of the compound (OR) having the general formula (II), wherein M is an alkali metal selected from the group consisting of Na, K and Li and x is 1 or M is an alkali-earth metal selected from the group consisting of Ca, Mg and Zn and x is 2; and $R_1$ is a hydrocarbon radical comprising from 10 to 22 carbon atoms, more preferably from 12 to 20 carbon atoms, even more preferably from 15 to 20 carbon atoms.

In yet another preferred embodiment, said composition (C) comprises relative to the total weight of the composition (C) from 50.0 wt. % to 65.0 wt. % of solid particles of the compound (OR) having the general formula (II), wherein M is a metal chosen from the group consisting of Na, Ca, Li, and mixtures thereof and x is 1 or 2; and $R_1$ is a hydrocarbon radical comprising from 15 to 20 carbon atoms.

Compound (I)

As detailed above, the composition (C) further comprises at least 25.0 wt. % and at most 75.0 wt. % of solid particles of at least one inert compound comprising at least C, H and O elements [compound (I), hereinafter] wherein said compound (I) has a density of below 2.4 g/cm$^3$ and a melting point of at least 40° C.

In the rest of the text, the expression "compound (I)" is understood, for the purposes of the present invention, both in the plural and the singular, that is to say that the composition (C) may comprise one or more than one compound (I).

According to a preferred embodiment of the present invention, the composition (C) comprises, relative to the total weight of the composition (C), the solid particles of the compound (I), as detailed above, in an amount of at least 30.0 wt. % or at least 35.0 wt. %. It is further understood that the solid particles of the compound (I) are advantageously present in the composition (C) in a weight amount of at most 70.0 wt. %, more preferably at most 60.0 wt. %, more preferably at most 55.0 wt. %, even more preferably at most 50.0 wt. %.

According to a preferred embodiment of the present invention, the composition (C) comprises, relative to the total weight of the composition (C), from 25.0 wt. % to 70.0 wt. %, preferably from 25.0 wt. % to 60.0 wt. %, more preferably from 30.0 wt. % to 50.0 wt. %, even more preferably from 35.0 wt. % to 50.0 wt. % of solid particles of the compound (I), as detailed above.

The compound (I), as detailed above, has the role as a modifier of bulk density and in part modifier of Zeff.

In this view, any compound (I) having a density of below 2.4 g/cm3 and a melting point of at least 40° C. is suitable to be combined with the compound (OR), as defined above, as long as the composition (C) to be formed, has a $Z_{eff}$ between 6.5 and 7.5.

Preferably, the compound (I) has a density of below 2.3 g/cm3, more preferably a density of below 2.2 g/cm$^3$, even more preferably a density of below 2.1 g/cm$^3$. It is to be understood that said compound (I) has advantageously a density of at least 0.8 g/cm$^3$, preferably a density of at least 0.9 g/cm$^3$, more preferably a density of at least 0.95 g/cm$^3$.

According to a preferred embodiment of the present invention, the compound (I) has a density from 0.8 g/cm$^3$ to 2.4 g/cm$^3$, preferably a density from 0.9 g/cm$^3$ to 2.3 g/cm$^3$, more preferably a density from 0.95 g/cm$^3$ to 2.2 g/cm$^3$, even more preferably a density from 0.95 g/cm$^3$ to 2.1 g/cm$^3$.

The density of the compound (I), as detailed above, is a property that can be measured according to standard methods in the art. A known method for measuring the density of compounds is notably according to the ISO 12154:2014 standard method which specifies a method for rapid and efficient determination of the skeleton density of solid material samples of regular or irregular shape, whether powdered or in one piece, by means of a gas displacement pycnometer.

Preferably, the density of the compound (I) is measured according to the ISO 12154:2014 standard method.

Preferably, the compound (I) has a melting point of at least 50° C., more preferably at least 55°, even more preferably at least 55° C. and most preferably at least 60° C.

It is further understood that within the context of the present invention the melting point of the compound (I), as detailed above, is a property that can be measured according to standard methods in the art. Known methods for measuring the melting point of compounds are notably the use of a capillary tube in a liquid bath, a capillary tube in a metal block, a Kofler hot bar, a melt microscope, differential thermal analysis (DTA), differential scanning calorimetry (DSC), freezing temperature, pour point etc.

Preferably, the melting point of the compound (I) is measured according to the ASTM D938 standard method.

As said, the compound (I) requires to comprise at least C, H and O elements.

Advantageously, the compound (I) comprises at least 5.0 wt. % of C elements, preferably at least 8.0 wt. % of C elements, more preferably at least 10.0 wt. % of C elements, relative to the total weight of the compound (I). It is further understood that the C elements are advantageously present in the composition (I) in a weight amount of at most 90.0 wt. %, preferably at most 80.0 wt. %, more preferably at most 70.0 wt. %, relative to the total weight of the compound (I).

According to certain embodiments of the present invention, the compound (I) comprises from 5.0 wt. % to 90.0 wt. % of C elements, preferably from 8.0 wt. % to 80.0 wt. % of C elements, more preferably from 10.0 wt. % to 70.0 wt. % of C elements, relative to the total weight of the compound (I).

Advantageously, the compound (I) comprises at least 1.0 wt. % of H elements, preferably at least 1.5 wt. % of H elements, more preferably at least 2.0 wt. % of H elements, relative to the total weight of the compound (I). It is further understood that the H elements are advantageously present in the composition (I) in a weight amount of at most 20.0 wt. %, preferably at most 15.0 wt. %, more preferably at most 13.0 wt. %, relative to the total weight of the compound (I).

According to certain embodiments of the present invention, the compound (I) comprises from 1.0 wt. % to 20.0 wt. % of H elements, preferably from 1.5 wt. % to 15.0 wt. % of H elements, more preferably from 2.0 wt. % to 13.0 wt. % of H elements, relative to the total weight of the compound (I).

Advantageously, the compound (I) comprises at 5.0 wt. % of O elements, preferably at least 8.0 wt. % of O elements, more preferably at least 12.0 wt. % of 0 elements, relative to the total weight of the compound (I). It is further understood that the O elements are advantageously present in the composition (I) in a weight amount of at most 70.0 wt. %, preferably at most 65.0 wt. %, more preferably at most 62.0 wt. %, relative to the total weight of the compound (I).

According to certain embodiments of the present invention, the compound (I) comprises from 5.0 wt. % to 70.0 wt. % of O elements, preferably from 8.0 wt. % to 65.0 wt. % of O elements, more preferably from 12.0 wt. % to 62.0 wt. % of O elements, relative to the total weight of the compound (I).

According to a preferred embodiment of the present invention, the compound (I) comprises at least 5.0 wt. % of C elements, at least 5.0 wt. % of O elements and at least 1.0 wt. % of H elements, relative to the total weight of the compound (I).

According to a more preferred embodiment of the present invention, the compound (I) comprises from 5.0 wt. % to 90.0 wt. % of C elements, from 5.0 wt. % to 70.0 wt. % of O elements and from 1.0 wt. % to 20.0 wt. % of H, relative to the total weight of the compound (I).

According to an even more preferred embodiment of the present invention, the compound (I) comprises from 8.0 wt. % to 80.0 wt. % of C elements, from 8.0 wt. % to 65.0 wt. % of O elements and from 1.5 wt. % to 15.0 wt. % of H elements, relative to the total weight of the compound (I).

According to most preferred embodiment of the present invention, said at least one compound (I) comprises from 10.0 wt. % to 70.0 wt. % of C elements, from 12.0 wt. % to 62.0 wt. % of O elements and from 2.0 wt. % to 13.0 wt. % of H elements, relative to the total weight of the compound (I).

Non-limiting examples of the compound (I) suitable for use in the composition (C) of the present invention, mention may be notably made of vanillin, caffeine, malic acid, sodium benzoate, glucose, sorbitol, xylitol, acetylsalicylic acid, ascorbic acid, cellulose, cyanuric acid, 2-amino-2-(hydroxymethyl)propane-1,3-diol, phenolic microspheres and their mixtures, preferably caffeine, malic acid, sodium benzoate, phenolic microspheres and their mixtures.

Within the context of present invention, the term "phenolic microspheres" is intended to denote hollow spheres made of a polyphenolic resin and having a particle size lower than 100 μm measured by dynamic image analysis.

Particle measurements by dynamic image analysis is known in the art. In this method, image analysis captures the physical properties of each single particle. The distribution of a property such as size or shape descriptor can thus be resolved in nearly any class. With image analysis even smallest amounts of over or under sized particles may be detected. Even single particles with specific geometric properties such as aggregates, fractures or foreign particles are traceable. Image analysis operates in a similar way to a modern microscope: a digital camera with special optics captures the particles within the frame. Physical information about particle properties is transmitted to a computer. For each single particle in the image size and shape descriptors are determined by evaluation software Phenolic microspheres made from phenol formaldehyde resin is notably described in US 2006/0160914 A1, such as for example phenol-formaldehyde-polymer hollow spheres.

In a preferred embodiment of the present invention, the composition (C) having a $Z_{eff}$ between 6.5 and 7.5, relative to the total weight of the composition (C), comprises:
a) from 40.0 wt. % to 65.0 wt. % of solid particles of the compound (OR), having the general formula (II):

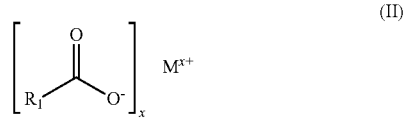

wherein M is an alkali metal selected from the group consisting of Na, K and Li and x is 1 or M is an alkali-earth metal selected from the group consisting of Ca, Mg and Zn and x is 2; and $R_1$ is a hydrocarbon radical comprising from 10 to 22 carbon atoms; and
b) from 35.0 wt. % to 60.0 wt. % of solid particles of the compound (I) wherein said compound (I) comprises from 8.0 wt. % to 80.0 wt. % of C elements, from 8.0 wt. % to 65.0 wt. % of O elements and from 1.5 wt. % to 15.0 wt. % of H elements, relative to the total weight of the compound (I) and has a density from 0.95 g/cm³ to 2.2 g/cm³ and a melting point of at least 60° C.

In a more preferred embodiment of the present invention, the composition (C) having a $Z_{eff}$ between 6.5 and 7.5, relative to the total weight of the composition (C), comprises:
a) from 50.0 wt. % to 70.0 wt. % of solid particles of the compound (OR), having the general formula (II):

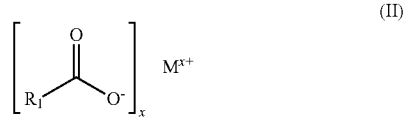

wherein M is an alkali metal selected from the group consisting of Na, K and Li and x is 1 or M is an alkali-earth metal selected from the group consisting of Ca, Mg and Zn and x is 2; and $R_1$ is a hydrocarbon radical comprising from 15 to 20 carbon atoms; and
b) from 30.0 wt. % to 50.0 wt. % of solid particles of the compound (I) wherein said compound (I) comprises from 10.0 wt. % to 70.0 wt. % of C elements, from 12.0 wt. % to 62.0 wt. % of O elements and from 2.0 wt. % to 13.0 wt. % of H elements, relative to the total weight of the compound (I) and has a density from 0.95 g/cm³ to 2.1 g/cm³ and a melting point of at least 60° C.

In a particular embodiment of the present invention, the composition (C) having a $Z_{eff}$ between 6.5 and 7.5, relative to the total weight of the composition (C), comprises:
a) from 50.0 wt. % to 70.0 wt. % of solid particles of an alkali metal or alkali-earth metal of stearate wherein the alkali metal is Na, K or Li and the alkali-earth metal is Ca, Mg or Zn; and
b) from 30.0 wt. % to 50.0 wt. % of solid particles of the compound (I) wherein said compound (I) is selected from the group consisting of vanillin, caffeine, malic acid, sodium benzoate, glucose, sorbitol, xylitol, acetylsalicylic acid, ascorbic acid, cellulose, cyanuric acid, 2-amino-2-(hydroxymethyl)propane-1,3-diol, phenolic microspheres and mixtures thereof.

Method for Producing the Composition (C)

A method for producing the composition (C), as detailed above, is also an aspect of the present invention.

Thus, according to the present invention there is provided a method for producing the composition (C), suitable for producing a simulant composition of an explosive compound [composition (S), hereinafter] having an effective atomic number [$Z_{eff}$, hereinafter] between 6.5 and 7.5, which method comprises the steps of blending, relative to the total weight of the composition (C),
a) at least 25.0% by weight (wt. %) and at most 75.0 wt. % of solid particles of the compound (OR) having the general formula (I):

wherein FG is a functional group selected from the group consisting of carboxylate group, a sulfate group, a sulfonate group, a benzylsulfonate ether groups, a phosphate group, an isethionate group, a sulphosuccinate group, an acyl citrate group, an acyl taurate group, an sarcosinate group, an amino carboxylate group; and wherein M is a metal M selected from the group consisting of alkali metals, alkali-earth metals and transition metals and x is 1, 2 or 3; and $R_1$ is hydrocarbon radicals comprising from 6 to 24 carbon atoms; and
b) at least 25.0% by weight (wt. %) and at most 75.0 wt. % of solid particles of the compound (I), as detailed above, wherein said compound (I) has a density of below 2.4 g/cm³ and a melting point of at least 40° C.

It is further understood that all the definitions, preferences and preferred embodiments hereinabove, also apply for all further embodiments, as described below.

Within the context of present invention, the term "blending" is intended to denote any combination or association of the solid particles of said compound (OR), as detailed above and the solid particles of the compound (I), as detailed above. The blending can be achieved by any blending method known by the skilled in the art. In general, blending of solid particles is carried out by intimate admixing of the constituent components in order to form a solid mixture. In the present invention, the blending is preferably carried out by first forming a slurry by admixing the solid particles of the compound (OR), as detailed above and the solid particles of the compound (I), as detailed above, with water followed by a step of drying this slurry. The drying step is typically carried out by using known techniques in the art, including for example rotatory evaporation, vacuum rotatory evaporation or oven drying, preferably oven drying.

Method for Producing the Composition (S)

Another aspect of the present invention is a method for producing the composition (S) having a $Z_{eff}$ between 6.5 and 7.5 and, as detailed above, by using the composition (C), as detailed above, wherein said method comprises the steps of:
c) subjecting the composition (C) to a size reducing step at a temperature below −50° C. in which the size of the solid particles of the compound (OR), as detailed above and the solid particles of the compound (I), as detailed above, comprised in the composition (C) are reduced to a volume average particle size X50 smaller or equal to 60 μm, thereby forming a mixture (1);
d) homogenizing the mixture (1) at a temperature between 15° C. to 35° C.; thereby forming a homogenized mixture (1); and e) compacting the homogenized mixture (1), thereby forming the composition (S) having a bulk density between 0.300 and 1.000 g/cm³.

Within the context of present invention, the $X_z$ notation with 0<z<100 represents a diameter, expressed in microns, relative to which z % in volume of particles are smaller relative to the total volume of particles.

For example, $X_{50}$ smaller or equal to 60 µm means that 50 volume % of the particles, relative to the total volume of particles, have a particle size smaller or equal to 60 µm.

The volume average particle size can be measured by dynamic image analysis (DIA), static laser light scatter-ing (SLS, also called laser diffraction) and sieve analysis, preferably by a dynamic image analysis dry method. Image analysis systems are known in the art. An example of image analysis systems include notably QICPIC (Sympatec GmbH).

According to the present invention, the size reducing step (c) of the composition (C) can be achieved by any method or technique known by the skilled in the art. Such techniques include for example: milling, crushing, cutting and grinding techniques, preferably milling. Milling techniques include for example: cryo-grinding vibrating milling, ball milling, edge or end runner milling, hammer milling, roller milling, mortar and pestle milling, or rotary cutter milling.

Preferably, the size reducing step (c) is carried out by cryo-grinding vibrating milling.

The size reducing step (c) of the composition (C) is performed at a low temperature in order to prevent any melting of the components during this step c) so that the obtained mixture (1) is in the form of a powder. Advantageously, the size reducing step (c) of the composition (C) is performed at a temperature below −70° C., preferably below −100° C., preferably below −120° C., more preferably below −140° C.

The inventors have found that when the volume average particle size X50 of the solid particles of the compound (OR), as detailed above and the solid particles of the compound (I), as detailed above, is too small, compaction of the mixture (1) might be difficult in view of the compound (OR) being an ionic compound having positively charged ions and negatively charged ions, as detailed above. Since the particle size of the solid particles affect the electrostatic interactions between said particles, it also means that it influences the bulk volume and thus the bulk density of mixtures comprising these particles. As a consequence, the volume average particle size X50 of the solid particles of the compound (OR), as detailed above and the solid particles of the compound (I), as detailed above, should be small enough in order to allow to reach the bulk density of the explosive compound.

Preferably, the size of the solid particles of the compound (OR), as detailed above and the solid particles of the compound (I), as detailed above, comprised in the composition (C) are reduced to a volume average particle size $X_{50}$ smaller or equal to 50 µm, more preferably smaller or equal to 40 µm, even more preferably smaller or equal to 30 µm. It is further understood that the size of the solid particles of the compound (OR), as detailed above and the solid particles of the compound (I), as detailed above, comprised in the composition (C) are advantageously reduced to a volume average particle size $X_{50}$ greater or equal to 5 µm, preferably greater or equal to 10 µm, even more preferably greater or equal to 15 µm.

In general, the size of the solid particles of the compound (OR), as detailed above and the solid particles of the compound (I), as detailed above, comprised in the composition (C) are reduced to a volume average particle size $X_{10}$ smaller or equal to 5 µm, preferably smaller or equal to 4 µm, more preferably smaller or equal to 3 µm. It is further understood that the size of the solid particles of the compound (OR), as detailed above and the solid particles of the compound (I), as detailed above, comprised in the composition (C) are reduced to a volume average particle size $X_{10}$ greater or equal to 1 µm, preferably greater or equal to 2 µm.

In general, the size of the solid particles of the compound (OR), as detailed above and the solid particles of the compound (I), as detailed above, comprised in the composition (C) are reduced to a volume average particle size $X_{90}$ smaller or equal to 160 µm, preferably smaller or equal to 150 µm, more preferably smaller or equal to 140 µm, even more preferably smaller or equal to 130 µm. It is further understood that the size of the solid particles of the compound (OR), as detailed above and the solid particles of the compound (I), as detailed above, comprised in the composition (C) are reduced to a volume average particle size $X_{90}$ greater or equal to 70 µm, preferably greater or equal to 80 µm.

According to a preferred embodiment of the present invention, the size of the solid particles of the compound (OR), as detailed above and the solid particles of the compound (I), as detailed above, comprised in the composition (C) are reduced to a volume average particle size $X_{50}$ between 10 µm and 50 µm, to a volume average particle size $X_{10}$ between 1 µm and 4 µm and to a volume average particle size $X_{90}$ between 70 µm and 150 µm.

According to a more preferred embodiment of the present invention, the size of the solid particles of the compound (OR), as detailed above and the solid particles of the compound (I), as detailed above, comprised in the composition (C) are reduced to a volume average particle size $X_{50}$ between 15 and 40 µm, to a volume average particle size $X_{10}$ between 2 and 3 µm and to a volume average particle size $X_{90}$ between 80 µm and 130 µm.

This being said, the particle size distribution of the solid particles of the compound (OR), as detailed above and the solid particles of the compound (I), as detailed above, comprised in the mixture (1) are characterized by a span value (SV) below 7, preferably below 6, more preferably below 5.5.

Within the context of present invention, the span value (SV) is defined as follows:

$$SV = \frac{(X_{90} - X_{10})}{X_{50}}$$

The span value characterizes the breadth of a particle size distribution. A small SV value means that the size distribution is narrow, while a large SV value means that the size distribution is broad.

The inventors have surprisingly found that when the particle size distribution of the solid particles of the compound (OR), as detailed above and the solid particles of the compound (I), as detailed above, comprised in the mixture (1) are narrow (small SV), particle stratification can be reduced or even avoided, which can result in simulant compositions with more controlled and homogeneous properties, particularly regarding density. This narrow particle distribution is thus helpful in order to produce simulant compositions that are even more similar to the explosive compound.

It was observed that the best results were obtained when SV is below 5.5.

In general, the particle size distribution of the solid particles of the compound (OR), as detailed above and the solid particles of the compound (I), as detailed above, comprised in the mixture (1) are characterized by a span value (SV) higher than 4.0, preferably higher than 5.0, more preferably higher than 4.5.

Accordingly the particle size distribution of the solid particles of the compound (OR), as detailed above and the solid particles of the compound (I), as detailed above, comprised in the mixture (1) are advantageously characterized by a span value (SV) between 4.0 and 7.0, preferably between 5.0 and 6.0, more preferably between 4.5 and 5.5.

As said, the mixture (1) is further subjected to a homogenizing step (d) at a temperature between 15° C. to 35° C., thereby forming a homogenized mixture (1).

Within the context of present invention, the term "homogenizing" is intended to denote any kind of intimate mixing known from the skilled in the art which increases the homogeneity of the mixture subjected to the homogenizing step d). Examples of homogenizing include shaking, 3D mixing, stirring, agitating.

Preferably, the homogenizing step is a shaking step, a 3D mixing step, a stirring step or an agitating step. More preferably, the homogenizing step is a 3D mixing step.

Within the context of present invention "a 3D mixing step" is intended to denote a mixing step using a 3D mixing device. The skilled in the art knows how to carry out a 3D mixing step. Examples of 3D mixing devices include DynaMIX CM200 (WAB, Basel, CH), PerMix PTU series 3D Mixer and JINHE® JHX. Generally, during a 3D mixing step, a mixture is placed inside a container which is sealed and then repeatedly rotated in different directions so as to increase the homogeneity of the mixture. The inventors used a mixing program comprising 12 rotations per minute on two axes to achieve the required 3D mixing.

As said, the homogenized mixture (1) is further subjected to a step of compaction (i.e. step e) in order reduce the bulk density of the homogenized mixture (1), thereby forming the composition (S) having an effective atomic number [$Z_{eff}$, hereinafter] between 6.5 and 7.5 and a bulk density between 0.300 and 1.000 g/cm$^3$.

Within the context of the present invention, the step of compaction can be performed by vibration compaction method known by the skilled in the art.

Typically, in the vibration compaction method, the particles are vibrator-packed into a compaction tube having a predefined length, in particular a plastic compaction tube having a predefined length.

In general, the homogenized mixture (1) is placed into the compaction tube which is attached to a vibrator and vibrated at 3000 vibrations per min. In between vibrating sequences, the compaction tube is dropped from a few cm to re-arrange the powder and facilitate compacting. The vibration is performed until the desired bulk density is obtained.

The bulk density is preferably measured using X-ray transmission, computer tomographic equipment, namely the Nuctech Kylin (Nuctech Company Limited, China), and/or Smiths XCT (Smiths Detection, Germany).

Preferably, the bulk density of the composition (S) is at least 0.400 g/cm$^3$, more preferably at least 0.500 g/cm$^3$, even more preferably at least 0.550 g/cm$^3$; On the other side, the bulk density of the composition (S) is preferably at most 0.900 g/cm$^3$, more preferably at most 0.800 g/cm$^3$.

More preferably, the bulk density of the composition (S) is between 0.400 and 1.000 g/cm$^3$, more preferably between 0.500 and 0.900 g/cm$^3$, even more preferably between 0.550 and 0.800 g/cm$^3$.

Another aspect of the present invention is a composition (S) which is a powdered simulant composition of an explosive compound having an $Z_{eff}$ between 6.5 and 7.5, and comprises based on the total weight of the composition (S),
a) from 25% by weight (wt. %) to 75 wt. % of solid particles of the compound (OR) having a volume average particle size $X_{50}$ smaller or equal to 60 µm, as detailed above; and
b) from 25% by weight (wt. %) to 75 wt. % of solid particles of the compound (I) having a density of below 2.4 g/cm$^3$, a melting point of at least 60° C. and having a volume average particle size $X_{50}$ smaller or equal to 60 µm, as detailed above; and
wherein the composition (S) has a bulk density between 0.300 and 1.000 g/cm$^3$.

It is further understood that all the definitions, preferences and preferred embodiments hereinabove, also apply for all further embodiments, as described below. Thus, the composition (S) may have all the features of composition (C), in particular in terms of particles size, SV, wt. % of the compound (OR), as detailed above and of the compound (I), as detailed above.

Another aspect of the present invention is the composition (S), obtained by the method

EXAMPLES

The invention will now be described in more details with examples, whose purpose is merely illustrative and not intended to limit the scope of the invention.

Raw Materials
Lithium stearate obtained from, Alfa Aesar, Germany
Calcium stearate obtained from, Alfa Aesar, Germany
Caffeine obtained from, Alfa Aesar, Germany
Sodium benzoate obtained from, VWR Chemicals, Belgium
Malic acid obtained from, Sigma Aldrich, Belgium 1. General Procedure for Producing the Composition (S)

A slurry was prepared by dissolving at least one compound (OR) and at least one compound (I) (the nature and the amount of each compound for example 1 and 2 are summarized in Table 1, below). The slurry was homogenized by mixing and was subsequently dried in a temperature controlled oven. The obtained powdered mixture was frozen overnight in liquid nitrogen in stainless steel container and was subsequently milled using a cryo-grinding vibrating mill. The mill was maintained below −120° C. throughout the process. The milled fractions were brought to room temperature in a dry atmosphere (this was achieved by displacing air with dry nitrogen gas) in order to avoid water condensation on the powder. The powder obtained was then homogenized in a 3D mixer (DynaMIX CM200 (WAB, Basel, CH)) for 1 hour. The homogenized mixture obtained was packed into a plastic tube of a predefined length and vibrated until the mixture had the desired volume. The excess of tube material was cut and the tube was sealed to ensure that the bulk density matches the target one.

Table 1, below summarizes the nature and weight percent of each compound for examples 1 and 2, the particles size characteristics of the solid particles in the homogenized mixture and the $Z_{eff}$ and the bulk density of the final mixture (i.e. composition (S)).

The particle size characteristics were measured according to dynamic image analysis method, using QICPIC analysis system (Sympathec GmbH).

The obtained particle size distribution of example 1 is shown in FIG. 1.

Figure 2:
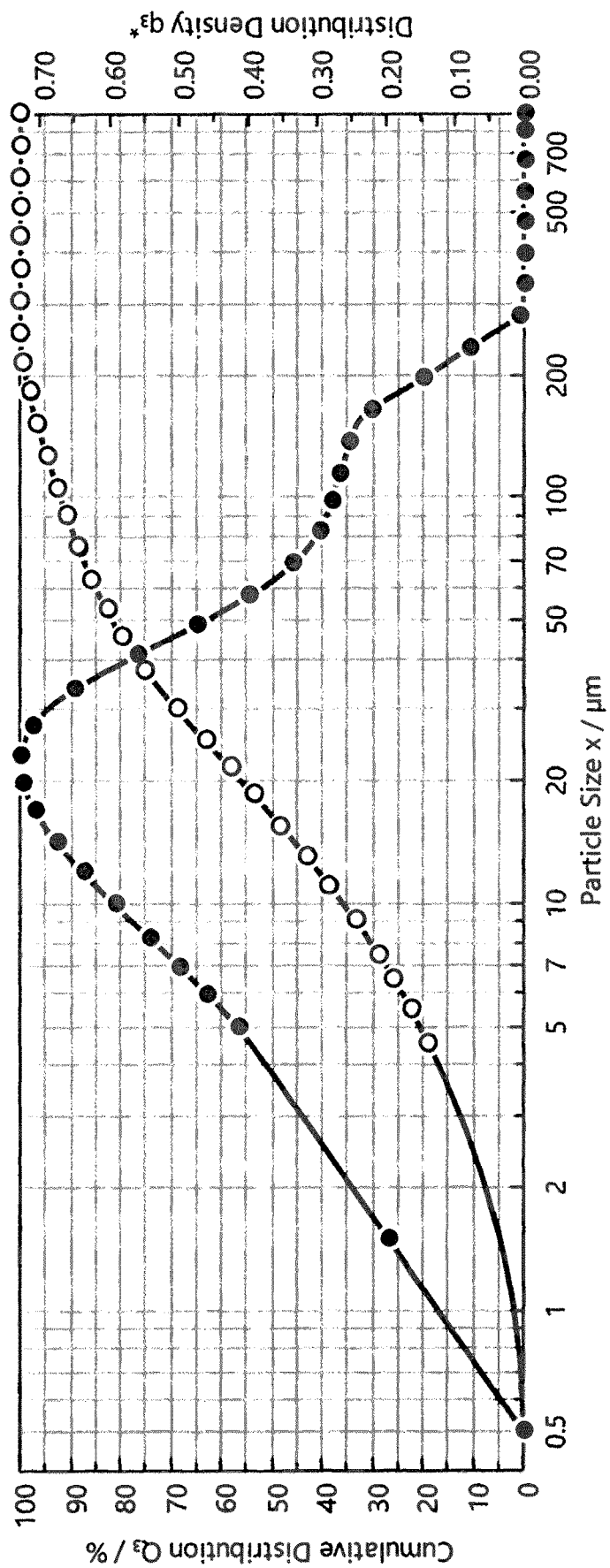
FIG. 2 shows the obtained particle size distribution of example 2.

The obtained particle size distribution of example 2 is shown in FIG. 2.

| Example Number | Ex 1 | Ex 2 |
|---|---|---|
| Lithium stearate (compound (OR)) | 42.9 wt. % | 53.9 wt. % |
| Calcium stearate (compound (OR)) | 2.8 wt. % | 10.2 wt. % |
| Caffeine (compound (I)) | 9.0 wt. % | |
| Sodium benzoate (compound (I)) | 45.3 wt. % | |
| Malic acid (compound (I)) | | 35.9 wt. % |
| Particle size Characteristics of the solid particles in the homogenized mixture | | |
| $X_{10}$ | 2.6 μm | 2.6 μm |
| $X_{50}$ | 16.5 μm | 16.5 μm |
| $X_{90}$ | 87.5 μm | 86.0 μm |
| Span value (SV) | 5.1 | 5.0 |
| Characteristics of the composition (S) | | |
| $Z_{\mathit{eff}}$ | 7.1 | 7.1 |
| Bulk density | 0.664 g/cm³ | 0.664 g/cm³ |

Thus, the composition (S) of examples 1 and 2 are good simulants of a TATP which are in the form of a white powder and which remain in the solid state at 60° C.

Furthermore, no self-compaction or particle stratification were observed for examples 1 and 2.

The invention claimed is:

1. A powdered composition suitable for producing a simulant composition of an explosive compound, said powdered composition having an effective atomic number between 6.5 and 7.5 and comprising, relative to the total weight of the powdered composition,
   a) at least 25.0% by weight (wt. %) and at most 75.0 wt. % of solid particles of at least one inert organic compound, having a general formula (I):

[R₁-FG]ₓMˣ⁺  (I)

wherein FG is a functional group selected from the group consisting of a carboxylate group, a sulfate group, a sulfonate group, a benzylsulfonate ether group, a phosphate group, an isethionate group, a sulphosuccinate group, an acyl citrate group, an acyl taurate group, an sarcosinate group, and an amino carboxylate group, wherein M is a metal selected from the group consisting of alkali metals, alkali-earth metals and transition metals and x is 1, 2 or 3, and wherein $R_1$ is a hydrocarbon radical comprising from 6 to 24 carbon atoms; and
   b) at least 25.0% by weight (wt. %) and at most 75.0 wt. % of solid particles of at least one inert compound (I) comprising at least C, H and O elements, wherein inert compound (I) has a density of below 2.4 g/cm3 and a melting point of at least 40° C.

2. The powdered composition according to claim 1, wherein the powdered composition comprises relative to the total weight of the powdered composition from 50.0 wt. % to 70.0 wt. % of solid particles of the inert organic compound, wherein the inert organic compound has the general formula (II):

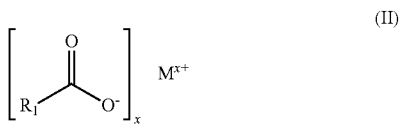

wherein M is an alkali metal selected from the group consisting of Na, K and Li and x is 1, or M is an alkali-earth metal selected from the group consisting of Ca, Mg and Zn and x is 2, and wherein $R_1$ is a hydrocarbon radical comprising from 10 to 22 carbon atoms.

3. The powdered composition according to claim 2, wherein $R_1$ is a hydrocarbon radical comprising from 12 to 20 carbon atoms.

4. The powdered composition according to claim 2, wherein $R_1$ is a hydrocarbon radical comprising from 15 to 20 carbon atoms.

5. The powdered composition according to claim 1, wherein the inert organic compound is sodium stearate, lithium stearate, calcium stearate, magnesium stearate, or zinc stearate or a mixture thereof.

6. The powdered composition according to claim 1, wherein inert compound (I) has a melting point of at least 60° C.

7. The powdered composition according to claim 1, wherein inert compound (I) comprises from 10.0 wt. % to 70.0 wt. % of C elements, from 12.0 wt. % to 62.0 wt. % of O elements and from 2.0 wt. % to 13.0 wt. % of H elements, relative to the total weight of inert compound (I).

8. The powdered composition according to claim 1, wherein inert compound (I) is selected from the group consisting of vanillin, caffeine, malic acid, sodium benzoate, glucose, sorbitol, xylitol, acetylsalicylic acid, ascorbic acid, cellulose, cyanuric acid, 2-amino-2-(hydroxymethyl) propane-1,3-diol, phenolic microspheres and their mixtures thereof.

9. A method for producing a simulant composition of an explosive compound having an effective atomic number between 6.5 and 7.5 by using the powdered composition, according to claim 1, wherein the method comprises the steps of:
   c) subjecting the powdered composition, according to claim 1, to a size reducing step at a temperature below −50° C. in which the size of the solid particles of the inert organic compound, and the solid particles of inert compound (I), comprised in the powdered composition are reduced to a volume average particle size $X_{50}$ smaller or equal to 60 μm, thereby forming a mixture;
   d) homogenizing the mixture at a temperature between 15° C. to 35° C.; thereby forming a homogenized mixture; and
   e) compacting the homogenized mixture, thereby forming the simulant composition of the explosive compound having a bulk density between 0.300 and 1.000 g/cm³.

10. The method for producing the simulant composition of the explosive compound having an effective atomic number between 6.5 and 7.5 according to claim 9, wherein the size reducing step (c) of the powdered composition is carried out by using a milling, a crushing, a cutting or a grinding technique.

11. The method for producing the simulant composition of the explosive compound having an effective atomic number between 6.5 and 7.5 according to claim 10, wherein the size reducing step (c) of the powdered composition is carried out by a milling technique.

12. The method for producing the simulant composition of the explosive compound having an effective atomic number between 6.5 and 7.5 according to claim 9, wherein the size reducing step (c) of the powdered composition is carried out by a milling technique selected from the group consisting of cryo-grinding vibrating milling, ball milling, edge or end runner milling, hammer milling, roller milling, mortar and pestle milling, and rotary cutter milling.

13. The method for producing the simulant composition of the explosive compound having an effective atomic number between 6.5 and 7.5 according to claim 12, wherein the size reducing step (c) of the powdered composition is carried out by a cryo-grinding vibrating milling technique.

14. The method for producing the simulant composition of the explosive compound having an effective atomic number between 6.5 and 7.5 according to claim 9, wherein the size of the solid particles of the inert organic compound, and the solid particles of inert compound (I), comprised in the powdered composition are reduced to a volume average particle size $X_{50}$ between 10 µm and 50 µm, to a volume average particle size $X_{10}$ between 1 µm and 4 µm and to a volume average particle size $X_{90}$ between 70 µm and 150 µm.

15. The method for producing the simulant composition of the explosive compound having an effective atomic number between 6.5 and 7.5 according to claim 9, wherein the particle size distribution of the solid particles of the inert organic compound and the solid particles of inert compound (I), comprised in the mixture are characterized by a span value (SV) below 7, and wherein the span value (SV) is defined according to following formula:

$$SV = \frac{(X_{90} - X_{10})}{X_{50}}.$$

16. The method for producing the simulant composition of the explosive compound having an effective atomic number between 6.5 and 7.5 according to claim 15, wherein the particle size distribution of the solid particles of the inert organic compound and the solid particles of inert compound (I), comprised in the mixture are characterized by a span value (SV) below 5.5, and wherein the span value (SV) is defined according to following formula:

$$SV = \frac{(X_{90} - X_{10})}{X_{50}}.$$

17. The method for producing the simulant composition of the explosive compound having an effective atomic number between 6.5 and 7.5 according to claim 9, wherein step e) is performed by a vibration compaction method.

18. A simulant composition of the explosive compound having an effective atomic number between 6.5 and 7.5, obtainable by the method according to claim 9.

19. A composition which is a powdered simulant composition of an explosive compound having an effective atomic number between 6.5 and 7.5, and comprising based on the total weight of the composition,
 a) from 25% by weight (wt. %) to 75 wt. % of solid particles of the inert organic compound, as defined according to claim 1, having a volume average particle size $X_{50}$ smaller or equal to 60 µm; and
 b) from 25% by weight (wt. %) to 75 wt. % of solid particles of inert compound (I), as defined according to claim 1, having a density of below 2.4 g/cm³, a melting point of at least 60° C. and having a volume average particle size $X_{50}$ smaller or equal to 60 µm; and
 wherein the composition has a bulk density between 0.300 and 1.000 g/cm³.

20. A method for producing a powdered composition, suitable for producing a simulant composition of an explosive compound having an effective atomic number between 6.5 and 7.5, wherein the method comprises the steps of blending, relative to the total weight of the powdered composition:
 a) at least 25.0% by weight (wt. %) and at most 75.0 wt. % of solid particles of an inert organic compound having the general formula (I):

$$[R_1\text{-FG}]_x M^{x+} \qquad (I)$$

wherein FG is a functional group selected from the group consisting of carboxylate group, a sulfate group, a sulfonate group, a benzylsulfonate ether group, a phosphate group, an isethionate group, a sulphosuccinate group, an acyl citrate group, an acyl taurate group, an sarcosinate group, and an amino carboxylate group, wherein M is a metal selected from the group consisting of alkali metals, alkali-earth metals and transition metals and x is 1, 2 or 3, and wherein $R_1$ is a hydrocarbon radical comprising from 6 to 24 carbon atoms; and
 b) at least 25.0% by weight (wt. %) and at most 75.0 wt. % of solid particles of inert compound (I), wherein inert compound (I) has a density of below 2.4 g/cm3 and a melting point of at least 40° C.

* * * * *